09-450 SB
11/18/86 RE 32,288

United States Patent [19]
Berger

[11] E Patent Number: Re. 32,288
[45] Reissued Date of Patent: Nov. 18, 1986

[54] HEAT TRAPPING COOKING GRILL

[75] Inventor: Bernard B. Berger, Aiken, S.C.

[73] Assignee: Ducane Heating Corporation, Columbia, S.C.

[21] Appl. No.: 775,408

[22] Filed: Sep. 12, 1985

Related U.S. Patent Documents

Reissue of:
[64] Patent No.: 9,131,983
Appl. No.: 210,916
Filed: Nov. 28, 1980

U.S. Applications:
[63] Continuation of Ser. No. 43,863, May 29, 1979, abandoned.

[51] Int. Cl. ..... A47J 37/08
[52] U.S. Cl. ..... 99/385; 99/450; 29/160
[58] Field of Search ..... 99/385, 393, 399, 415, 99/417, 418, 422, 427, 445, 447, 450; 126/25 R, 25 A, 39 E, 39 M, 214 C, 299 A, 299 D, 152 B, 152 R, 332, 336; 29/160; 52/667

[56] References Cited

U.S. PATENT DOCUMENTS

| | | |
|---|---|---|
| 265,391 | 10/1882 | Cottingham . |
| 894,711 | 7/1908 | Worcester . |
| 1,014,684 | 1/1912 | Weygand . |
| 1,233,795 | 7/1917 | Krebs . |
| 1,838,732 | 12/1931 | Bates . |
| 2,420,112 | 5/1947 | Utzler . |
| 2,539,243 | 7/1951 | Brown . |
| 2,856,502 | 10/1958 | Wolf . |
| 3,152,586 | 10/1964 | Russell . |
| 3,220,400 | 11/1965 | Yager . |
| 3,353,527 | 11/1967 | Anderson . |
| 3,369,481 | 2/1968 | Pappas . |
| 3,443,510 | 5/1969 | Norton . |
| 3,446,361 | 5/1969 | Douty . |
| 3,555,994 | 1/1971 | Nemetz et al. . |
| 3,566,585 | 3/1971 | Voloshen et al. . |
| 3,623,936 | 11/1971 | Hotz . |
| 3,717,083 | 2/1973 | Karapetian . |
| 3,800,777 | 4/1974 | Gebien . |
| 3,982,476 | 9/1976 | McLane . |

FOREIGN PATENT DOCUMENTS

| | | |
|---|---|---|
| 827946 | 11/1969 | Canada . |

*Primary Examiner*—Lowell A. Larson
*Attorney, Agent, or Firm*—Pollock, Vande Sande & Priddy

[57] ABSTRACT

The cooking grill disclosed has a series of inverted U-shaped channels for trapping hot convection gases beneath a substantially flat cooking surface. The channels are held together by one or more cross stringers which pass through sidewalls of each channel in apertures adjacent to a channel base and are secured to the channel base by securing means of various types. Sidewalls may be flared and exterior surfaces coated with an easily cleaned material. The stringers may be of various cross sections.

32 Claims, 7 Drawing Figures

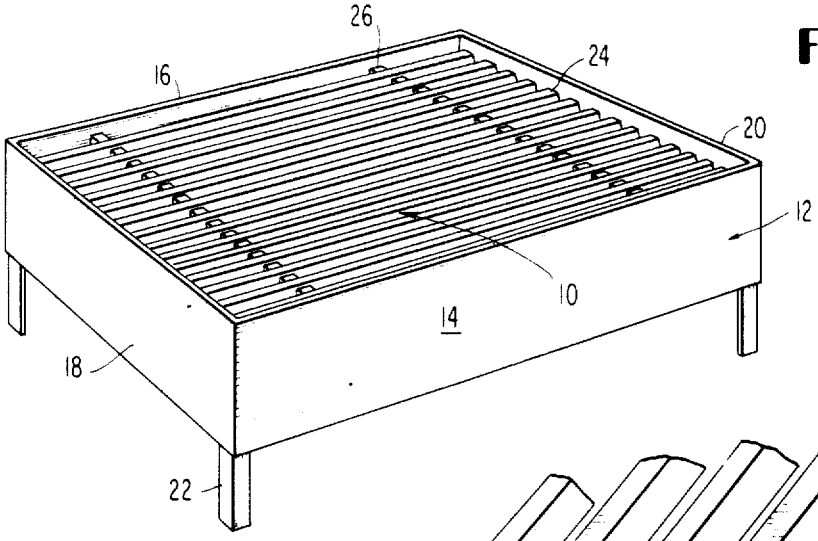
FIG. 1
FIG. 2
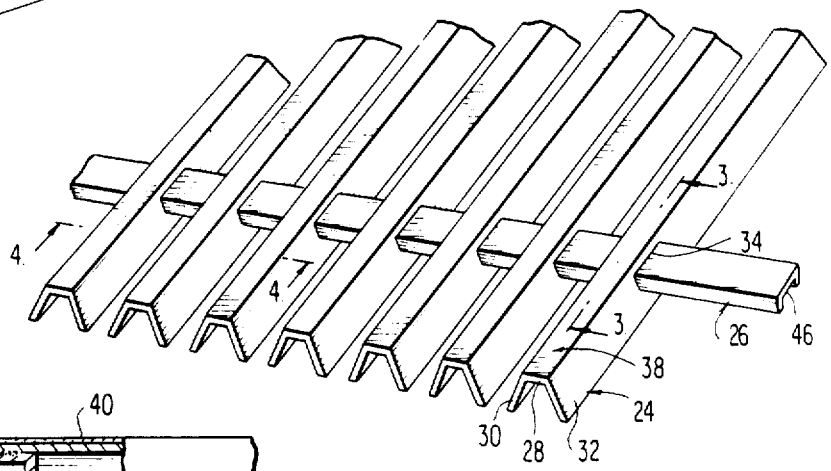
FIG. 3
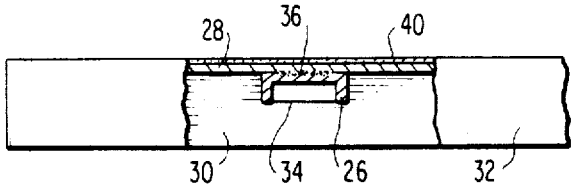
FIG. 4
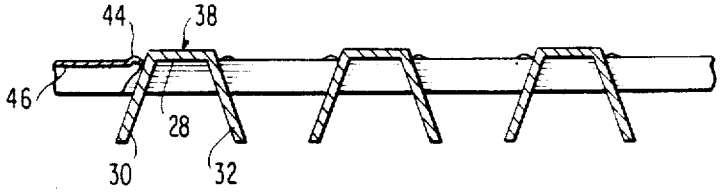
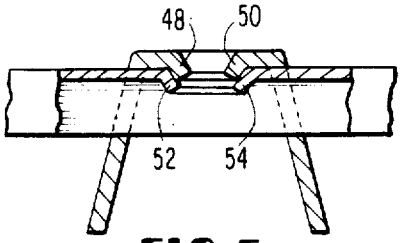
FIG. 5
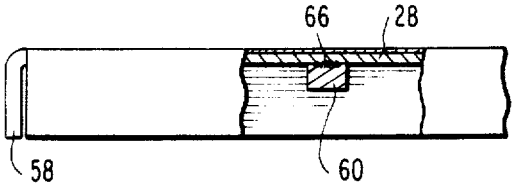
FIG. 6
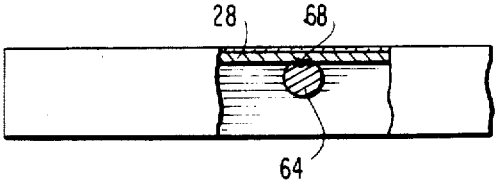
FIG. 7

HEAT TRAPPING COOKING GRILL

Matter enclosed in heavy brackets [ ] appears in the original patent but forms no part of this reissue specification; matter printed in italics indicates the additions made by reissue.

This is a continuation of application Ser. No. 43,863 filed May 29, 1979, now abandoned.

TECHNICAL FIELD

The present invention relates generally to lattice type shelves for supporting food within a cooking unit and more particularly to an improved construction for cooking grills of the type employed in portable outdoor cooking units. The invention is especially useful for gas-fired barbecue units.

BACKGROUND ART

In conventional barbecue units, the cooking or food supporting grill is usually suspended directly over a suitable source of heat, such as charcoal or a gas burner with intervening ceramic briquets. The heat source may also be exposed electrical resistance elements as well known in the art. Cooking or barbecue units of these types usually employ rod-type grillwork fabricated from wire rods arranged in parallel and spot welded to a peripheral stringer and one or more cross stringers.

One of the problems encountered with such prior art grills is that they allow practically all of the convective heat which does not come into direct contact with overlying foodstuffs to escape upwardly without transferring significant cooking heat to the food. It is also desirable when barbecuing to leave distinctive sear marks on the foodstuff being cooked, especially meats. The narrow rods of the prior art usually do not become hot enough to actually sear the food material and when such rods can be heated sufficiently, they produce a very narrow sear mark which is not attractive in appearance.

Although cooking grids with inverted U-shaped channels are found in the prior art as illustrated in U.S. Pat. No. 3,369,481 to Pappas, such grids in the past have been fabricated from cast iron. These grids are extremely heavy and easily broken or cracked if inadvertently dropped or subjected to rapid changes in temperature. Both cast iron grids and wire-type grills are relatively expensive to manufacture and quickly become corroded and unsightly in use. Furthermore, these cooking structures are difficult to clean which enhances their unsightly appearance and promotes corrosive action by the retained food drippings.

DISCLOSURE OF THE INVENTION

What is needed is a sturdy but resilient cooking grill capable of trapping and utilizing convective heat to cook and sear the surface of supported foodstuffs. It is therefore a principal object of the present invention to provide such an improved cooking grill for cooking units that depend at least in part upon hot convection gases for cooking food.

Another object of the invention is to provide a cooking grill having inverted channels for trapping rising hot air and combustion products beneath a cooking surface to reduce heat loss and increase the cooking surface temperature.

Yet another object of the invention is the provision of heat trapping grill members of heat conducting material, such as metal, so that heat trapped away from supported foodstuff is transmitted by conduction to cooking surfaces in contact with food material.

A further object of the invention is the provision of an elongated grill member having a wide, substantially flat upper cooking surface for producing a distinctive sear mark on the food being cooked.

Other features of the invention include a grill that can be fabricated either from corrosion resistant materials that cannot be readily molded or from materials susceptible to corrosion which can be easily and economically coated with porcelain enamel or some other corrosion resistant material. The coatings applied also serve as smooth, non-absorbing or non-stick surfaces for easy cleaning and maintenance. Although a significant portion of the heat is trapped beneath grill members, the spacing between adjacent members is still sufficient to allow flavoring smoke and vapors to impinge directly upon the foodstuff so as to impart the usual charcoal or barbecue flavor.

The present invention has the further advantages of providing a tough, resilient structure capable of resisting damage from accidental impacts and rapid temperature changes and which is simple and economical to manufacture. The component parts of the grill can be cut and shaped from standard metal stock and easily assembled with relatively few tools and production steps.

The foregoing objectives are accomplished by a cooking grill comprised of individual channel members having an inverted U-shaped cross section and secured together by transverse stringers which are threaded through apertures in the sidewalls of each channel member. The apertured construction of the channels permits the use of a variety of stringer designs and fastening arrangements in manufacturing the composite grill. The grill is arranged to be positioned over and in vertically spaced relation to a source of cooking heat with the open side of each U-shaped channel facing downwardly so that each channel forms an inverted pocket which traps rising hot air and combustion products. The base of the inverted channel has a wide, substantially flat upper cooking surface for supporting and searing the underside of foodstuff resting thereon. The exterior surfaces of the channel are preferably coated with a vitreous or non-stick material and the sidewalls flared outwardly to facilitate cleaning. The flared sidewalls also assist in trapping heat in the transverse space therebetween. Adjacent channels are spaced transversely apart to provide open spaces allowing a portion of the heated convection gases to pass freely through the grill for flavoring the cooking food. A novel cooking grill is thus provided which optimizes cooking, searing, and flavoring of the foodstuff and which is easily cleaned after the cooking operation has been completed.

In addition to the numerous advantages apparent from the foregoing discussion, the invention provides a practical and efficient grill for supporting food in a wide variety of cooking units, such as barbecue grills, open hearth grills and other types of cooking assemblies with a convective-type heat source. The exact nature of the invention, as well as other objects and advantages, will be readily apparent from the annexed drawing and the following specific description of the preferred embodiments of the invention.

BRIEF DESCRIPTION OF DRAWINGS

For a better understanding of the present invention, reference is made to the accompanying drawing in which:

FIG. 1 is a perspective view of a portable barbecue unit employing the novel cooking grill of the present invention.

FIG. 2 is a perspective fragmentary view showing a portion of the novel cooking grill.

FIG. 3 is a front elevation in fragmentary section taken along line 3—3 of FIG. 2 and shows structural details of the stringer to channel connection.

FIG. 4 is a side elevation in fragmentary section taken along 4—4 of FIG. 2 and shows structural details of a modification in the stringer to channel connection.

FIG. 5 is a side elevation in fragmentary section similar to FIG. 4 and shows structural details of yet another modification in the channel to stringer connection.

FIG. 6 is a front elevation in fragmentary section similar to FIG. 3 and shows additional stringer and channel modifications.

FIG. 7 is a front elevation in fragmentary section similar to FIG. 6 and shows still another stringer modification.

BEST MODE FOR CARRYING OUT THE INVENTION

Referring now to the drawing, particularly to FIGS. 1, 2 and 3, there is illustrated one form of cooking grill made according to the present invention. The cooking grill, generally designated 10, is positioned within and extends across the open top of a barbecue grill housing 12 having a front wall 14, a rear wall 16, a pair of side walls 18 and 20, and four supporting legs 22, each at one corner of the housing. As shown best in FIG. 2, the cooking grill is comprised of a plurality of elongated channel members 24 arranged in parallel spaced relation and secured together by two or more cross stringers 26. Each channel has an inverted U-shaped cross section comprised of a base 28 and depending sidewalls 30 and 32. Each sidewall contains an aperture 34 for receiving stringer 26 which may be spot welded to the inside of channel base 28 as at 36 in FIG. 3. Although one or both sidewalls may intersect the channel base at an angle of 90 degrees or less, the opposing sidewalls of each channel are preferably flared outwardly from base to edge at an angle of approximately 10 to 35 degrees on either side of vertical. In the preferred construction, the upper edge of the apertures in the sidewalls is immediately adjacent to the inner surface of the channel base to provide abutting contact between the base and the upper surface of the stringer. This feature facilitates resistance welding and the like. The outer surface of the base of each channel is substantially flat to form a cooking surface 38. Both the cooking surface and the outer surface of the depending sidewalls are preferably coated with an easily cleaned coating 40 as shown best in FIGS. 3 and 4. This coating may be a vitreous material such as porcelain enamel or a non-stick material such as that sold under the trademark Teflon. The sidewalls of stringer 26 may also be flared outward and its outer surfaces similarly coated. All of these surfaces will be referred to collectively as exterior surfaces.

When in use, the cooking grill is mounted adjacent to the top edge of the cooking unit and extends horizontally so as to hold foodstuff over a source of cooking heat (not shown) mounted in the lower portion of the housing. The cooking area of the unit is defined by a composite upper grill surface formed by the flat cooking surfaces of the individual channel members. The cooking grill 10 is preferably mounted within the housing 12 in a detachable fashion. Conventional mountings can be used and may be comprised of a ledge running along the inside surface of each housing wall. The sidewall ledges can engage the lower edge of each channel member at its outer ends to each side and the front and rear wall ledges can engage the lower edge of each cross stringer at its outer ends to the front and rear. Two or more projecting lugs may be used on each wall instead of a ledge, with each sidewall lug engaging the end of a channel member on the underside of its base and each front and rear lug similarly engaging the end of each stringer. It is to be understood that the convection heat for the grill may be supplied by either gas burners or burning charcoal supported in the bottom portion of the housing. A coal grate assembly may also be suspended within the housing to support a bed of ceramic or refractory briquets between gas burners and the grill. In this way, burning gas can also provide a source of radiant cooking heat as described in the inventor's prior U.S. Pat. No. 3,989,028 of Nov. 2, 1976, which patent is incorporated herein by reference. Although the channel members are shown extending horizontally from side to side, they may of course extend from front to rear and be mounted in an inclined position instead.

With reference to FIG. 4 of the drawing, there is shown a modification of the invention wherein the stringers are detachably secured to the channel members by means of locking dimples or detents 44 pressed into the upper run 46 of the stringer. A detent on each side of the channels secures the stringer against axial movement by frictionally engaging an adjacent outer surface of opposing sidewalls 30 and 32. Detents may instead by pressed or punched from the channel sidewalls and received in recesses similarly formed in the stringer. In either case, the engagement is such that normal loading will not depress the detents but the detents can be released by firmly pulling the stringer axially through the apertures. This allows the component parts of the grill to be separated for cleaning.

In FIG. 5 of the drawing there is illustrated another modification of the invention wherein the individual channels are attached to the stringer by a mechanical punching operation that locks the two parts together by punching tabs 48 and 50 out of the channel base and interlocking tabs 52 and 54 out of the abutting portion of the stringer. The heating trapping function of the channels may be further enhanced by similarly forming an end wall 58 at the ends of the channel as illustrated in FIG. 6. However, the invention operates satisfactorily without any end walls since in their absence most of the convection gases leaving the channel pocket will still spill over around the lower edges of the sidewalls. This is especially the case where the channel ends are at least partially blocked by abutting walls of the housing enclosure as seen in FIG. 1. Open ended channels without any blockage are also effective and may be inclined slightly in the longitudinal direction to induce convection flow of trapped gases along the channel from the lower to the higher end. In some cases, this flow may actually increase the transfer of heat energy from the gases to the channel material.

The modification of FIG. 6 also illustrates the use of solid bar stock having a rectangular cross-section for the stringer 60. A similar modification is shown in FIG. 7 where a solid wire stringer 64 of round cross-section is used for securing the channel members together. The modified cross stringers are preferably secured to the inner surface of the channel base by welding 66 and 68, respectively, although other means of attachment, such as those illustrated in FIGS. 4 and 5, may be used.

Each of the cross stringers disclosed can be formed from standard channel or bar stock materials. The channel members are preferably formed from standard flat stock such as low carbon steel strips or sheets. To form a channel, an elongated strip of the desired length is first punched with transverse apertures appropriately spaced to yield sidewall apertures for receiving the cross stringers, and then stamped into the flaired U-shaped channel having the cross-section shown in the drawing. The vitreous or non-stick coating may be applied to exterior channel and stringer surfaces either before or after assembly of the grill structure. However, when using electric resistance welding to fasten the channels to the stringers, it is preferable to coat exterior surfaces of both parts after they have been secured together. Where the parts have been coated earlier, the types of connections illustrated in FIGS. 4 and 5 can be used or other welding techniques can be employed, such as projection welding, at each transverse juncture. Since the method of manufacture utilizes preformed stock of the type that can be extruded instead of cast or rolled, both the channels and the stringers may be fabricated from corrosive resistant materials such as aluminum and other extruded metals or certain high temperature extruded plastics. Where plastics are used, solvent melding or high temperature adhesives may be employed instead of welding or punching techniques.

The width of the base portion and the transverse spacing of channel members relative to each in the grill assembly are pertinent features of the invention. Where the heat source is burning gas or charcoal, the channels should be spaced transversely apart by a distance sufficient to allow combustion products to escape without smothering of the burning fuel. Where ceramic briquets are heated to incandescence by the burning gas and used to incinerate drippings and sauces falling from the cooking food, the open space between channels permits flavoring smoke and vapors generated by such incineration to impinge directly upon the food and thereby impart the characteristic charcoal or barbecued flavor. A portion of the convection heat and radiant energy generated by the heat source also passes through the same open space and either impinges upon the cooking food or escapes. On the other hand, a larger portion of the area on the underside of the grill is taken up by the composite channel area represented by the sum of the areas of each channel as defined by the lower edges of its sidewalls. This composite channel area traps a substantial portion of the rising hot air and combustion products and a major portion of any radiant energy, the former proportion depending on the size of the channel pocket and convection flow in and out of the channel and the latter proportion being a function of the covered surface area. Another spacing consideration is that the upper cooking surfaces of adjacent channels should be sufficiently close to support food with relatively little cohesiveness, such as hamburger patties. This prevents food being cooked on the grill from coming apart and falling through the open spaces. The foregoing spacing objectives can be achieved by spacing the lower edges of each channel transversely apart from the lower edge of the next adjacent channel by a distance approximately equal to the width of the channel's upper cooking surface as illustrated best in FIG. 4.

INDUSTRIAL APPLICABILITY

The cooking grill assembly of the present invention can be used in a wide variety of cooking unit designs, both portable and fixed and of the indoor and outdoor type. Although it can be used with electrical units having uncovered radiant coils, the grill is best used with combustion heat sources of the gas-fired or charcoal type since these have a larger proportion of convection gases. By trapping a significant portion of those gases and a major portion of any radiant energy associated therewith, the channels are heated to a relatively high and substantially uniform temperature. The temperature of the flat cooking surface on the upper side of the channel is sufficiently high to sear abutting food surfaces during the cooking operation. Furthermore, heat energy trapped at remote locations is transmitted to those portions of the cooking surface in contact with the food thereby making use of heat that would otherwise be lost and utilizing the heat source more efficiently.

The cooking grill is of relatively lightweight and rugged construction and can be economically manufactured from the standard metal stock materials. The composite structure provides a relatively large area of flat cooking surface for supporting and heating the food to be cooked. The relatively wide strip of cooking surface on each channel produces wide sear marks of distinctive and pleasing appearance on the cooked food. The underside of each channel base provides a relatively large lateral dimension for fastening individual channels together by means of a transverse stringer or strut. Because heated gases tend to rise, the trapped gases flow within the confines of each channel until the channel is filled and then spill around the lower edges thereof into the open spaces between channels in a manner that helps distribute both the heat and flavoring vapors evenly over the entire cooking surface of the grill.

It should be readily apparent from the above that the cooking grill of the present invention is not limited to the specific modes described. Thus, only a few embodiments have been presented and other embodiments and variations will occur to those skilled in the art. Furthermore, many structural changes are possible and those changes are intended to be within the scope of this disclosure. For example, other channel shapes may be employed, such as flattened semi-oval shapes or M-shapes. In addition, punched tabs and detachable detents of various other shapes and sizes can be used to fasten the channel members to the cross stringers.

The invention therefore may be embodied in other specific forms without departing from the essential features and characteristics disclosed. The present embodiments are to be considered in all respects as illustrative and not restrictive, the scope of the invention being defined by the claims below rather than by the above description. All changes coming within the meaning and range of equivalents to those features described in the claims are intended to be embraced in the invention.

What is claimed is:

1. A cooking grill for supporting food to be cooked over heating means for providing cooking heat, said cooking grill comprising:

a plurality of elongated channel members spaced transversely apart one adjacent to the other and each comprising a deformable sheet of heat conducting material deformed to provide a transversely and longitudinally extending base and opposing, longitudinally extending sidewalls depending from said base and diverging from each other from said base to the lower edge of each sidewall, said base being substantially flat in both said transverse and said longitudinal directions and defining a wide, substantially flat cooking surface extending transversely across and longitudinally along the upper side of said base, and said base and said opposing sidewalls defining an inverted channel pocket beneath said base, the transverse width of said channel pocket between the lower edges of said opposing sidewalls being significantly greater than the transverse width of said base and said channel pocket providing a trap for a sufficient portion of said cooking heat to cause said wide, substantially flat cooking surface to sear abutting surfaces of food supported over said heating means by said channel member;

at least one set of apertures comprised of an aperture extending through each sidewall adjacent to said substantially flat base of each of said adjacent channel members;

at least one elongated stringer passing through said at least one set of apertures and extending between the opposing sidewalls of each of said adjacent channel members; and, securing means for securing the base of each of said channel members to said stringer extending between said opposing sidewalls so as to hold said channel members in said transversely spaced adjacent relationship.

2. The cooking grill of claim 1 in which said channel members are transversely spaced relative to each other so that the composite channel area defined by the sum of the areas beneath said inverted channel pockets is greater than the composite open area between the lower edges of the sidewalls of adjacent channel members.

3. The cooking grill of claim 1 in which said sidewalls diverge outwardly by at least 10° relative to a plane normal to the plane of said substantially flat channel base.

4. The cooking grill of claim 2 in which said channel members have a substantially uniform cross-section and are arranged with their substantially flat cooking surfaces in substantially the same plane, the longitudinal axes of said elongated channel members are substantially parallel, and the transverse spacing between the lower edges of the sidewalls of adjacent channel members is approximately equal to the transverse width of said substantially flat channel base.

5. The cooking grill of claim 1 in which said stringer is comprised of an elongated sheet of deformable material having a major cross-sectional dimension transverse to the longitudinal axis of said elongated stringer, said major cross-sectional dimension defining a substantially flat stringer surface, and in which said substantially flat stringer surface extends in the longitudinal direction of each of said elongated channel members and abuts the underside of said substantially flat channel base.

6. The cooking grill of claim 5 which said securing means includes a welded connection between said stringer and said channel base.

7. The cooking grill of claim 5 in which said securing means includes a deformed portion of said stringer engaging a deformed portion of said channel base.

8. The cooking grill of claim 5 in which said securing means includes locking means for detachably securing said stringer within the apertures of said sidewalls.

9. The cooking grill of claim 8 in which said locking means comprises a pair of detents carried by said stringer and arranged to frictionally engage the opposing sidewalls of said channel member.

10. A method of manufacturing a cooking grill which comprises the steps of:

piercing at least two transversely spaced apertures in an elongated sheet of heat conducting, deformable material;

deforming said elongated sheet along two longitudinally extending lines of deformation to form an elongated channel member having a transversely and longitudinally extending base and opposing, longitudinally extending sidewalls projecting outward from one side of said base and diverging from each other from said base to the outer edge of each sidewall, said base being substantially flat in both said transverse and said longitudinal directions and defining a wide, substantially flat cooking surface extending transversely across and longitudinally along the side of said base opposite to said one side from which said sidewalls project, said base and said opposing sidewalls defining a channel pocket on said one side of said base, and said lines of deformation being selected so that each of said sidewalls contains one of said at least two transversely spaced apertures;

threading an elongated stringer through said at least two transversely spaced apertures so that a portion of said stringer extends between the opposing sidewalls of said channel member, said stringer being sufficiently long to receive a plurality of said channel members in transversely spaced relation;

positioning a plurality of said elongated channel members in transversely spaced relation on said stringer with said wide, substantially flat cooking surface positioned upwardly and said opposing sidewalls projecting downwardly so that said channel pocket is inverted, the transverse width of said channel pocket between the outer edges of said opposing sidewalls being significantly greater than the transverse width of said base and said inverted channel pocket when supported over a source of cooking heat providing a trap for a sufficient portion of said cooking heat to cause said wide, substantially flat cooking surface to sear abutting surfaces of food supported over said heat source by said channel members; and, securing the base of each of said channel members to said elongated stringer so as to retain said channel members in said transversely spaced adjacent relationship and provide means for supporting said plurality of channel members over a source of cooking heat.

11. The method of claim 10 which further includes an additional step of coating the exterior surface of said channel with a vitreous or a non-stick material.

12. The method of claim 10 in which said securing step includes welding said channel base to said stringer portion lying within said sidewalls.

13. The method of claim 10 in which said securing step includes deforming said channel members or said stringer so that said stringer frictionally engages each of said channel members.

14. The method of claim 10 in which said securing step includes deforming both the base of said channel members and the portion of said stringer lying within said sidewalls so that said stringer lockingly engages each of said channel members.

*15. A cooking grill for supporting food to be cooked over heating means for providing cooking heat, said cooking grill comprising:*

*a plurality of elongated channel members spaced transversely apart one adjacent to the other and each comprising a deformable sheet of heat conducting material deformed to provide a transversely and longitudinally extending base and opposing, longitudinally extending sidewalls depending from said base and diverging from each other from said base to the lower edge of each sidewall, said base being substantially flat in both said transverse and said longitudinal directions and defining a wide, substantially flat cooking surface extending transversely across and longitudinally along the upper side of said base, and said base and said opposing sidewalls defining an inverted channel pocket beneath said base, the transverse width of said channel pocket between the lower edges of said opposing sidewalls being significantly greater than the transverse width of said base and said channel pocket providing a trap for a sufficient portion of said cooking heat to cause said wide, substantially flat cooking surface to sear abutting surfaces of food supported over said heating means by said channel member; and,*

*at least one elongated stringer connected to each of said channel members so as to hold said channel members in said transversely spaced adjacent relationship, said at least one stringer having a base and opposing sidewalls depending from said stringer base so as to define an inverted stringer pocket for trapping a portion of said cooking heat beneath said stringer base.*

*16. The cooking grill of claim 15 in which the sidewalls of said at least one stringer are flared outwardly from said stringer base.*

*17. The cooking grill of claim 15 in which said at least one stringer has an exterior upper surface and exterior sidewall surfaces, and each of said channel members has an exterior upper surface and exterior sidewall surfaces; and in which said exterior surfaces are coated with a vitreous or a non-stick material.*

*18. The cooking grill of claim 15 in which said at least one stringer has an inverted U-shaped cross-section.*

*19. The cooking grill of claim 15 in which said at least one stringer is of heat conducting material.*

*20. The cooking grill of claim 15 comprising a plurality of said stringers.*

*21. A cooking grill for supporting food to be cooked over heating means for providing cooking heat, said cooking grill comprising:*

*a plurality of elongated channel members spaced transversely apart one adjacent to the other and each comprising a deformable sheet of heat conducting material deformed to provide a transversely and longitudinally extending base and opposing, longitudinally extending sidewalls depending from said base and diverging from each other from said base to the lower edge of each sidewall, said base being substantially flat in both said transverse and said longitudinal directions and defining a wide, substantially flat cooking surface extending transversely across and longitudinally along the upper side of said base, and said base and said opposing sidewalls defining an inverted channel pocket beneath said base, the transverse width of said channel pocket between the lower edges of said opposing sidewalls being significantly greater than the transverse width of said base and said channel pocket providing a trap for a sufficient portion of said cooking heat to cause said wide, substantially flat cooking surface to sear abutting surfaces of food supported over said heating means by said channel member;*

*at least one elongated stringer extending between the sidewalls of said adjacent channel members; and,*

*securing means for securing each of said channel members to said at least one stringer to hold said channel members in said transversely spaced adjacent relationship.*

*22. The cooking grill of claim 21 in which each of said channel sidewalls is provided with an aperture and said at least one elongated stringer passes through said apertures.*

*23. The cooking grill of claim 21 or 22 in which said securing means comprises means for engaging said channel base.*

*24. The cooking grill of claim 23 in which said stringer abuts the underside of the base of each of said adjacent channel members.*

*25. The cooking grill of claim 21 or 22 in which said securing means comprises means for engaging a sidewall of each of said adjacent channel members.*

*26. The cooking grill of claim 25 in which said securing means includes a pair of detents carried by said stringer and arranged to frictionally engage the opposing sidewalls of said channel members.*

*27. The cooking grill of claim 21 or 22 in which said channel members are transversely spaced relative to each other so that the composite channel area defined by the sum of the areas beneath said inverted channel pockets is greater than the composite open area between the lower edges of the sidewalls of adjacent channel members.*

*28. The cooking grill of claim 21 or 22 in which said channel sidewalls diverge outwardly by at least 10° relative to a plane normal to the plane of said substantially flat channel base.*

*29. The cooking grill of claim 21 or 22 in which said channel members have a substantially uniform cross-section and are arranged with their substantially flat cooking surfaces in substantially the same plane, and the longitudinal axes of said elongated channel members are substantially parallel.*

*30. The cooking grill of claim 21 or 22 which comprises a plurality of said stringers.*

*31. The cooking grill of claim 21 or 22 in which each channel base has an exterior upper surface and each channel sidewall has an exterior side surface, in which said at least one stringer has exterior surfaces extending between the exterior side surfaces of adjacent channel members, and in which said exterior surfaces are coated with a vitreous or a non-stick material.*

*32. The cooking grill of claim 21 in which each of said channel sidewalls is provided with an aperture and said at least one elongated stringer passes through said apertures, said channel sidewalls diverge outwardly by at least 10° relative to a plane normal to the plane of said substantially flat channel base, and said channel members are transversely spaced relative to each other so that the composite channel area defined by the sum of the areas beneath said inverted channel pockets is greater than the composite open area between the lower edges of the sidewalls of adjacent channel members.*

* * * * *

UNITED STATES PATENT AND TRADEMARK OFFICE

CERTIFICATE OF CORRECTION

PATENT NO. : Re. 32,288

DATED : Nov. 18, 1986

INVENTOR(S) : Bernard B. Berger

It is certified that error appears in the above-identified patent and that said Letters Patent is hereby corrected as shown below:

On the title page, please change the patent number of the parent patent from "9,131,983" to --4,403,541--.

Signed and Sealed this

Seventeenth Day of February, 1987

*Attest:*

DONALD J. QUIGG

*Attesting Officer*

*Commissioner of Patents and Trademarks*